United States Patent [19]
Gosch et al.

[11] Patent Number: 4,990,688
[45] Date of Patent: Feb. 5, 1991

[54] REMOVAL OF CYCLOHEXANOL

[75] Inventors: Hans-Juergen Gosch, Durkheim; Rolf Fischer, Heidelberg, both of Fed. Rep. of Germany

[73] Assignee: BASF Aktiengesellschaft, Ludwigshafen, Fed. Rep. of Germany

[21] Appl. No.: 383,057

[22] Filed: Jul. 21, 1989

[30] Foreign Application Priority Data

Aug. 27, 1988 [DE] Fed. Rep. of Germany ....... 3829142

[51] Int. Cl.$^5$ ............................................. C07C 29/86
[52] U.S. Cl. .................................... 568/810; 568/835
[58] Field of Search ............... 568/810, 834, 835, 868, 568/895, 899, 913

[56] References Cited

U.S. PATENT DOCUMENTS

| | | | |
|---|---|---|---|
| 2,927,944 | 3/1960 | Giesen et al. | 568/835 |
| 2,974,174 | 3/1961 | Edmiston | 568/835 |
| 4,306,101 | 12/1981 | Slaugh et al. | 568/835 |
| 4,691,064 | 9/1987 | Shirafuji et al. | 568/835 |
| 4,849,551 | 7/1989 | Shirafuji et al. | 568/913 |

FOREIGN PATENT DOCUMENTS

| | | | |
|---|---|---|---|
| 0123713 | 11/1984 | European Pat. Off. | 568/835 |
| 227931 | 7/1987 | European Pat. Off. | 568/835 |
| 0285911 | 10/1988 | European Pat. Off. | 568/835 |
| 62-103033 | 5/1987 | Japan | 568/835 |

Primary Examiner—Werren B. Lone
Attorney, Agent, or Firm—Keil & Weinkauf

[57] ABSTRACT

Cyclohexanol is removed from aqueous solutions containing it and aromatic sulfonic acid by extraction using as the extractant a mixture of (a) one or more liquid aliphatic, cyloaliphatic or aromatic hydrocarbons, halohydrocarbons or ethers which are inert under extraction conditions and
(b) one or more phenols.

6 Claims, No Drawings

REMOVAL OF CYCLOHEXANOL

European Patent Application 123,713 discloses a process wherein cyclohexanol is obtained by hydrating cyclohexene at from 50° to 200° C. in from 5 to 80% by weight strength solutions of aromatic sulfonic acids in water. To prevent corrosion, the reaction is carried out for example in the presence of heteropoly acids, salts or oxidants of molybdenums, tungsten or vanadium. The cyclohexanol formed by hydration of cyclohexene predominantly dissolves in the aqueous phase, which contains the aromatic sulfonic acid, and is mostly not removed therefrom even by excess cyclohexene.

JP-A2-103,033/1987 recommends aliphatic, cycloaliphatic and aromatic hydrocarbons for extracting cyclohexanol from aqueous solutions of aromatic sulfonic acids. However, appreciable amounts of extractants are necessary to obtain effective extraction. Industrially, this is very expensive.

In a process described in European Patent Application 227,931, the hydration of cyclohexene is carried out in aqueous solutions of aromatic sulfonic acids with one or more hydroxyl groups on the aromatic ring and the cyclohexanol is subsequently extracted with aromatic hydrocarbons. It is true that with this process it is possible to reduce the amount of extractant, but the use of hydroxyl-containing aromatic sulfonic acids substantially reduces the yield of and selectivity for cyclohexanol.

It is an object of the present invention to improve the removal of cyclohexanol from aqueous aromatic sulfonic acid solutions as obtained in the hydration of cyclohexene in the presence of aromatic sulfonic acids.

We have found that this object is achieved by a process for removing cyclohexanol from aqueous solutions containing it and aromatic sulfonic acids by extraction using as the extractant a mixture of
(a) one or more liquid aliphatic, cycloaliphatic or aromatic hydrocarbons, halohydrocarbons or ethers which are inert under extraction conditions and
(b) one or more phenols.

The novel process has the advantage that the amount of extractant to be used is appreciably reduced and a better extraction result is obtained. This is even true if hydroxyl-free sulfonic acids are used as hydrating agents in the preparation of cyclohexanol, which additionally increases the yield of cyclohexanol.

According to the invention, the starting point is an aqueous solution which contains cyclohexanol and an aromatic sulfonic acid in solution. A solution of this type is obtained in the hydration of cyclohexene to cyclohexanol by reacting cyclohexene in an aqueous solution which contains from 5 to 80% by weight of an aromatic sulfonic acid, in particular a benzene- or naphthalene-sulfonic acid, which may be substituted, such as benzenesulfonic acid, toluenesulfonic acid or naphthalenesulfonic acid, or dodecylbenzenesulfonic acid, at from 50° to 200° C., in particular from 70° to 150° C., under from 1 to 10 bar. It is advantageous to use in addition molybdenic acid or a salt thereof, vanadium oxide or a vanadate in an amount of for example from 0.001 to 5% by weight, based on the aromatic sulfonic acid. In addition, it is also advisable to use a heteropoly acid such as phosphorusmolybdenic acid, phosphorus-tungstenic acid, phosphorusmolybdenictungstic acid or phosphorusmolybdenicvanadic acid. Suitable processes are described for example in European Patent 123,713 and European Patent Application 206,631. The resulting reaction mixture separates into an organic phase comprising excess cyclohexene, which contains minor amounts of cyclohexanol, and an aqueous phase typically composed for example of from 5 to 10% by weight of cyclohexanol, from 40 to 70% by weight of aromatic sulfonic acid and from 20 to 50% by weight of water. The cyclohexene phase can be separated off, by example by decanting, and worked up separately. However, it is not absolutely necessary to separate off the cyclohexene before the extraction since it can be utilized as an additional extractant as will be described hereinafter.

The aqueous solution thus obtained is extracted with an extractant mixture of
(a) one or more liquid aliphatic, cycloaliphatic or aromatic hydrocarbons, halohydrocarbons or ethers which are inert under extraction conditions and
(b) one or more phenols.

Suitable hydrocarbons have in general from 6 to 12 carbon atoms, examples being benzene, toluene, cyclohexene, decalin or tetralin. Suitable halohydrocarbons have in general 1 or 2 carbon atoms, for example fluoro-chloro-, or bromo-hydrocarbons, in particular chlorohydrocarbons, e.g. methylene chloride, chloroform, dichlorethane, dichlorethylene or carbon tetrachloride. Soluble ethers have in general from 6 to 12 carbon atoms. It is possible to use for example diphenyl ether or cyclohexyl ether. It is particularly advantageous to use cyclohexyl ethers such as dicyclohexyl ether, cyclohexyl methyl ether, cyclohexyl ethyl ether, cyclohexyl n-propyl ether, cyclohexyl i-propyl ether, cyclohexyl n-butyl ether, cyclohexyl i-butyl ether or phenyl cyclohexyl ether.

Suitable phenols are for example monocyclic, dicyclic or tricyclic phenols which have up to 3 hydroxyl groups and may additionally have alkyl radicals of from 1 to 15 carbon atoms, alkoxy radicals of from 1 to 4 carbon atoms or halogen atoms such as chlorine or bromine as substituents. Suitable phenols are for example phenol, o-, m- or p-alkylphenols such as cresols, xylenols, trimethylphenols, ethylphenols, tertiarybutylphenols, tertiaryamylphenols, nonylphenols, 4-methyl-2,6-ditertiarybutylphenol, 2-tertiarybutylmethylphenol, 2,5-ditertiarybutylhydrophenol, phenylphenol, chlorophenols, hydroquinone, resorcinol, pyrocatechol, pyrogallol, hydroquinone monomethyl ether and mixtures thereof. Particular importance has been attained by monocyclic phenols having up to 2 hydroxyl groups and up to 3 alkyl groups, each of up to 15 carbon atoms, as substituents.

In general, the extractant contains from 0.1 to 90% by weight of one or more phenols. Particularly suitable amounts are from 5 to 50% by weight, in particular from 10 to 40% by weight.

For every part by volume of the aqueous solution of aromatic sulfonic acid and cyclohexanol to be extracted it is advantageous to use from 0.1 to 50 parts by volume, in particular from 1 to 10 parts by volume, of extractant mixture. The extraction in general is carried out at from 0° to 200° C., advantageously from 10° to 100° C., in particular from 10° to 50° C.

The extraction of the aqueous solution with its cyclohexanol and aromatic sulfonic acid content can be carried out batchwise by mixing the aqueous solution intensively with the phenol-containing extractant and subsequently separating the phases. Advantageously, the extraction is carried out continuously in countercurrent in suitable extraction columns such as stirred disk columns, pulsed columns or single- or multi-stage mixer settlers. The aqueous phase obtained, which still contains the aromatic sulfonic acid, is reused for the hydration of cyclohexene, while the cyclohexanol-containing extractant phase is worked up by distillation. Small amounts of phenols which in the course of the phase separation pass into the aqueous aromatic sulfonic acid phase do not interfere with the hydration. If small amounts of aromatic sulfonic acids end up in the cyclohexanol-containing extract, they are easily removable by washing with a little water and are advantageously added to the aqueous hydrating solution.

In a preferred embodiment of the extraction process, an extractant is used which has a higher boiling point than cyclohexanol by a sufficient margin for economical separation, for example >10° C. In this case, it is only necessary to separate the cyclohexanol from the extractant by distillation. The extractant obtained as the bottom phase is advantageously recycled into the extraction stage. In a preferred embodiment, the extraction is carried out using the excess cyclohexene phase obtained in the hydration. The subsequent workup thus gives first a cyclohexene fraction, which is reused for the hydration, a cyclohexanol fraction and, as the bottom product, the extractant.

The cyclohexanol obtainable by the process of the invention is suitable for preparing cyclohexanone, an important starting material for caprolactam.

The process according to the invention is illustrated by the Examples following. The parts by weight bear the same relation to parts by volume as the kilogram to the liter.

EXAMPLE 1

17.4 parts by volume of an aqueous solution of 54 parts by weight of p-toluenesulfonic acid, 10 parts by weight of cyclohexanol and 36 parts by weight of water were intensively mixed with 22.9 parts by volume of a solution of 15% by weight of 4-nonylphenol in toluene in a vessel on a shaking machine at room temperature for 5 minutes. After phase separation it was found by gas used has been extracted from the aqueous phase by the phenol/toluene solution.

EXAMPLES 2–9

The extraction was carried out as described in Example 1, except that the extractant used were various phenols, each in solution in toluene. The results are shown in Table 1.

TABLE 1

| Example | Phenol | Conc. of phenol [% by weight] | Extracted cyclohexanol [% by weight] |
|---|---|---|---|
| 2 | phenol | 15 | 22.7 |
| 3 | 4-methylphenol | 15 | 22.8 |
| 4 | 4-tert-butylphenol | 10 | 29.1 |
| 5 | 4-tert-amylphenol | 15 | 30.2 |
| 6 | 2-tert-butyl-4-methylphenol | 15 | 41.6 |
| 7 | 2,6-di-tert-butylphenol | 10 | 16.6 |
| 8 | 2,6-di-tert-butyl-4-methylphenol | 10 | 17.0 |
| 9 | 2,5-di-tert-butylhydroquinone | 2 | 19.1 |

EXAMPLES 10–12

The extraction was carried out as described in Example 1, except that an aqueous solution of 64 parts by weight of p-toluenesulfonic acid, 10 parts by weight of cyclohexanol and 26 parts by weight of water was used and a 15% strength by weight solution of various phenols in toluene was used as extractant. The results are shown in Table 2.

TABLE 2

| Example | Phenol | Conc. of phenol [% by weight] | Extracted cyclohexanol [% by weight] |
|---|---|---|---|
| 10 | 4-tert-amylphenol | 15 | 16.1 |
| 11 | 4-nonylphenol | 15 | 28.1 |
| 12 | 2-tert-butyl-4-methylphenol | 15 | 25.1 |

EXAMPLES 13–18

The extraction was carried out as described in Example 1, except that in each case a 15% strength by weight solution of one of the following phenols in one of various hydrocarbons was used as extractant. The results are shown in Table 3.

TABLE 3

| Example | Hydrocarbons and ethers | Extracted cyclohexanol [% by weight] 2tB4m[1] | Extracted cyclohexanol [% by weight] 4Nonyl[2] |
|---|---|---|---|
| 13 | cyclohexene | 47.0 | — |
| 14 | toluene | 41.6 | 44.5 |
| 15 | tetralin | 41.0 | 45.1 |
| 16 | decalin | 34.8 | 47.6 |
| 17 | 4-tert-butyltoluene | 38.9 | — |
| 18 | dicyclohexyl ether | 35.6 | — |

[1] 2tB4m = 2-tert-butyl-4-methylphenol
[2] 4Nonyl = 4-nonylphenol

EXAMPLES 19–22

The extraction was carried out as described in Example 1, except that the aqueous phase used was a solution of 64 parts by weight of p-toluenesulfonic acid, parts by weight of cyclohexanol and 26 parts by weight of water and the extractant used was a 15% strength by weight solution of one of the stated phenols in one of various hydrocarbons. The results are shown in Table 4.

TABLE 4

| Example | Extractant | Extracted cyclohexanol [% by weight] 2tB4m | Extracted cyclohexanol [% by weight] 4Nonyl |
|---|---|---|---|
| 19 | toluene | 24.5 | 28.1 |
| 20 | tetralin | 25.8 | 25.6 |
| 21 | decalin | 18.6 | 31.7 |
| 22 | 4-tert-butyltoluene | 23.4 | 32.0 |

EXAMPLES 23–27

To demonstrate the continuous form of extraction, an aqueous solution of 54 parts by weight of p-toluenesulfonic acid, 10 parts by weight of cyclohexanol and 36 parts by weight of water was continuously extracted in a 5-stage mixer settler with a solution of 15% by weight of 2-tert-butyl-4-methylphenol in tetralin at room temperature. In each Example, the ratio of aqueous solution to extractant was varied. The residence time in the apparatus was from 1.3 to 2.2 hours. The amount of extracted cyclohexanol was determined by gas chromatography. The results are shown in Table 5.

TABLE 5

| Example | Volume ratio of aqueous solution to extractant | Residence time [h] | Extracted cyclohexanol [% by weight] |
|---|---|---|---|
| 23 | 1:7 | 1.5 | 99 |
| 24 | 1:3.7 | 1.3 | 99 |
| 25 | 1:2.6 | 1.3 | 98 |
| 26 | 1:2 | 1.4 | 86 |
| 27 | 1:1 | 2.2 | 46 |

EXAMPLE 28

In a pressure vessel made of glass, 320 parts by weight of 60% strength aqueous p-toluenesulfonic acid and 32 parts by weight of cyclohexene per hour were reacted with one another at 118° C. and 5 bar. The two-phase mixture was intensively stirred at 800 rpm during the reaction in the reactor. Downstream of the reactor, the unconverted cyclohexene was separated off in a phase with its cyclohexanol content was transferred into a 5-stage separator and the aqueous p-toluenesulfonic acid phase mixer settler. In the mixer settler, the substantially cyclohexene-free reaction mixture was continuously extracted with a 15% strength by weight solution of 2-tert-butyl-4-methylphenol in tetralin. The volume ratio of aqueous solution to extractant was 1:2.3 and the residence time was 1.3 hours. After the aqueous and organic phases had been separated, the organic phase, which following passage through the mixer settler contained cyclohexanol, was passed into a falling film evaporator combined with a packed column. The aqueous p-toluenesulfonic acid solution was returned into the hydration stage after water which had been consumed in the course of the reaction had been added back. Operating at an evaporator temperature of 115° C., a pressure of 30 mbar and a reflux ratio of 1:5, the distillate obtained at the top of the column was composed of 64% by weight of cyclohexanol, 12% by weight of water, 14% by weight of cyclohexene and 9% by weight of tetralin. The evaporator bottom product was a cyclohexanol-freed phenol/tetralin solution, which was reused for the cyclohexanol extraction.

The run continued over a period of 100 hours. During this period, the average cyclohexene conversion was 53 mol % and the cyclohexanol selectivity 97%. The average cyclohexanol yield was 51.5 mol %.

COMPARATIVE EXAMPLES 1-5

The extraction was carried out as described in Example 1, except that in each case the pure hydrocarbons were used for the extraction. The results are shown in Table 6.

TABLE 6

| Comparative Example | Extractant | Extracted cyclohexanol [% by weight] |
|---|---|---|
| 1 | cyclohexene | 13.7 |
| 2 | toluene | 16.4 |
| 3 | tetralin | 14.4 |
| 4 | decalin | 5.2 |
| 5 | 4-tert-butyltoluene | 11.6 |

COMPARATIVE EXAMPLES 6-9

The extraction was carried out as indicated in Comparative Example 1, except that the aqueous phase used was a solution of 64% by weight of p-toluenesulfonic acid, 10% by weight of cyclohexanol and 26% by weight of water. The results are shown in Table 7.

TABLE 7

| Comparative Example | Extractant | Extracted cyclohexanol [% by weight] |
|---|---|---|
| 6 | toluene | 9.8 |
| 7 | tetralin | 9.2 |
| 8 | decalin | 2.9 |
| 9 | 4-tert-butyltoluene | 6.7 |

COMPARATIVE EXAMPLE 10

The extraction was carried out continuously as described in Examples 23-27. Pure toluene was used for the extraction in place of phenol/tetralin solution. The volume ratio of the aqueous phase to toluene was 1:5 and the residence time was 1.5 hours. Under these conditions, 62% of cyclohexanol was extracted from the aqueous phase.

We claim:

1. In a process for removing cyclohexanol from an aqueous solution containing cyclohexanol and an aromatic sulfonic acid by extraction, the improvement comprising bringing the solution into contact with an extractant comprising a mixture of:
   (a) one or more liquid aliphatic, cycloaliphatic or aromatic ethers which are inert under extraction conditions, and
   (b) one or more phenols.

2. A process as defined in claim 1, wherein the ether is selected from the group consisting of diphenyl ether, dicyclohexyl ether, cyclohexyl methyl ether, cyclohexyl ethyl ether, cyclohexyl n-propyl ether, cyclohexyl i-propyl ether, cyclohexyl n-butyl ether, phenyl cyclohexyl ether, and mixtures thereof.

3. A process as defined in claim 1, wherein the ether is dicyclohexyl ether.

4. A process as defined in claim 1, wherein from 1 to 10 parts by volume of extractant are used per part by volume of aqueous solution.

5. A process as defined in claim 1, wherein the extractant contains from 5 to 50% by weight of one or more phenols.

6. A process as defined in claim 1, wherein the extractant has a higher boiling point than cyclohexanol.

* * * * *